(12) United States Patent
Kehn

(10) Patent No.: US 9,371,335 B2
(45) Date of Patent: Jun. 21, 2016

(54) SPIROTHIENOPYRAN-PIPERIDINE DERIVATIVES AS ORL-1 RECEPTOR ANTAGONISTS FOR THEIR USE IN THE TREATMENT OF ALCOHOL DEPENDENCE AND ABUSE

(71) Applicant: Eli Lilly and Company, Indianapolis, IN (US)

(72) Inventor: Linda Rorick Kehn, New Palestine, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/357,825

(22) PCT Filed: Nov. 29, 2012

(86) PCT No.: PCT/US2012/066918
§ 371 (c)(1),
(2) Date: May 13, 2014

(87) PCT Pub. No.: WO2013/085781
PCT Pub. Date: Jun. 13, 2013

(65) Prior Publication Data
US 2014/0309251 A1 Oct. 16, 2014

Related U.S. Application Data

(60) Provisional application No. 61/567,242, filed on Dec. 6, 2011.

(51) Int. Cl.
| | | |
|---|---|---|
| *A61K 31/44* | (2006.01) | |
| *C07D 495/20* | (2006.01) | |
| *A61K 31/435* | (2006.01) | |
| *A61K 31/452* | (2006.01) | |

(52) U.S. Cl.
CPC ............ *C07D 495/20* (2013.01); *A61K 31/435* (2013.01); *A61K 31/452* (2013.01)

(58) Field of Classification Search
CPC .................................................... A61K 31/452
USPC ................................................. 514/278, 811
See application file for complete search history.

(56) References Cited

U.S. PATENT DOCUMENTS 5,140,032 A * 8/1992 Radecki ........................ 514/221

FOREIGN PATENT DOCUMENTS

| EP | 1873150 A1 | 1/2008 |
| WO | 2011060035 A1 | 5/2011 |
| WO | 2011060217 A1 | 5/2011 |

OTHER PUBLICATIONS

Daina Economidou et al., Dysregulation of Nociceptin/Orphanin FQ Activity in the Amygdala is Linked to Excessive Alcohol Drinking in the Rat, Biol Psychiatry (2008) 64: 211-218.
L.-C. Chiou et al., Nociceptin/Orphanin FQ Peptide Receptors: Pharmacology and Clinical Implications, Current Drug Targets (2007) 8: 117-135.
Olivier Civelli, The Orphanin FQ/Nociceptin (OFQ/N) System, Results Probl Cell Differ (2008) 46: 1-25.
Niall P. Murphy, The Nociceptin/Orphanin FQ System as a Target for Treating Alcoholism, CNS & Neurological Disorders—Drug Targets, (2010) 9: 87-93.
Alexander Kuzmin et al., The Nociceptin/Orphanin FQ Receptor Agonist Ro 64/6198 Reduces Alcohol Self-Administration and Prevents Relapse-Like Alchol Drinking, Neuropsychopharmacology (2007) 32: 902-910.
D. Economidou et al., Effect of novel nociceptinlorphanin FQ-NOP receptor ligands on ethanol drinking in alcohol-preferring msP rats, Peptides (2006) 27: 3299-3306.
Roberto Ciccocioppo et al., Attenuation of ethanol self-administration and of conditioned reinstatement of alcohol-seeking behaviour by the antiopioid peptide nociceptin/orphanin FQ in alcohol-preferring rats, Psychopharmacology (2004) 172: 170-178.
Rainer K. Reinscheid, The Orphanin FQ / Nociceptin Receptor as a Novel Drug Target in Psychiatric Disorders, CNS & Neurological Disorders—Drug Targets (2006) 5: 219-224.
Nurulain T. Zaveri, The Nociceptin/Orphanin FQ Receptor (NOP) as a Target for Drug Abuse Medications, Current Topics in Medicinal Chemistry (2011) 11: 1151-1156.

* cited by examiner

*Primary Examiner* — Kevin E Weddington
(74) *Attorney, Agent, or Firm* — R. Craig Tucker

(57) ABSTRACT

The use of ORL-1 receptor antagonists of the formula:

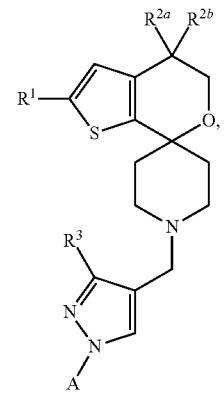

for the treatment of alcohol use disorders is described.

14 Claims, No Drawings

SPIROTHIENOPYRAN-PIPERIDINE DERIVATIVES AS ORL-1 RECEPTOR ANTAGONISTS FOR THEIR USE IN THE TREATMENT OF ALCOHOL DEPENDENCE AND ABUSE

This U.S. national stage application of International Application PCT/US2012/066918, filed Nov. 29, 2012, claims priority to U.S. provisional application Ser. No. 61/567,242, filed Dec. 6, 2011.

The present invention relates to the use of Nociceptin/orphanin FQ receptor (NOC/OFQ) antagonists, specifically ORL-1 receptor antagonists, for the treatment of alcohol use disorders.

Alcohol use disorders, such as alcohol dependence and alcohol abuse, present a significant health and social problem. The World Trade Organization (WTO) has identified alcohol use disorders as the "third leading risk factor for premature deaths and disabilities in the world". Approximately 2.5 million people die annually from alcohol-related causes worldwide, with roughly 10% of deaths occurring in individuals less than 30 years of age. Harmful use of alcohol accounts for approximately 4.5% of global disease burden, as measured in disability-adjusted life years lost, and is a major risk factor for neuropsychiatric diseases and other health problems, such as cardiovascular disease, cirrhosis of the liver and cancers of the mouth, larynx, pharynx, esophagus, breast, and bowel. The current standards of care are naltrexone and acamprosate, which help patients maintain abstinence by reducing alcohol cravings and by blocking the rewarding aspects of alcohol when it is consumed. However, currently available treatments do little to treat comorbid mood disorders. In fact, naltrexone can produce anhedonia in some individuals. As such, there is a need for improved pharmaceutical therapeutics to treat alcohol use disorders.

The Nociceptin/orphanin FQ receptor (NOC/OFQ), specifically the ORL-1 receptor, is a Class A G-protein coupled receptor (GPCR) that is expressed primarily in the central nervous system and peripheral nervous system as well as in the gastrointestinal tract, smooth muscle, and immune system. While related structurally to opioid receptors, the OFQ/Nociceptin system exhibits no significant cross reactivity to the classical opioid receptors, mu, delta, and kappa. Moreover, nociceptin exhibits anti-opioid activity in vivo (e.g. ORQ/Nociceptin, the natural ligand for ORL-1 receptor, has been reported to exhibit anti-nociceptive properties).

Nociceptin/orphanin FQ receptor (NOC/OFQ) antagonists, specifically antagonists of the ORL-1 receptor have demonstrated anti-depressant like activity and anorectic activity in several animal models for depression and feeding behavior. As such, ORL-1 antagonists are deemed to be useful in the treatment of depression and/or the treatment of overweight, obesity, and/or weight maintenance post treatment for overweight or obesity. Other studies suggest possible use of antagonists in the treatment of pain, dementia and Parkinsonism. Nociceptin/orphanin FQ receptor (NOC/OFQ) agonists on the other hand have been implicated for the treatment of alcohol use disorders, anxiety, pain, stress induced anorexia, cough, neurogenic bladder, edema, and drug dependence. (see e.g. Murphy, Niall P. (2010), The Nociceptin/Orphanin FQ System as a Target for Treating Alcoholism. CNS & Neurological Disorders—Drug Tartgets 9:87-93.; and Chiou, L. C., Liao, Y. Y., Fan, P. C., Kuo, P. H., Wang, C. H., Riemer, C. and Prinssen, E. P. (2007), Nociceptin/Orphanin FQ Peptide Receptors: Pharmacology and Clinical Implications. Current Drug Targets 8:117-135.)

WO 2011/060035 and WO 2011/060217 describe certain spiropiperidine compounds as ORL-1 antagonists for use in the treatment of depression, overweight, obesity, weight maintenance and migraine.

Unexpectedly, we have now discovered that ORL-1 antagonist compounds may be useful in the treatment of alcohol use disorders, as for example in the treatment of alcohol abuse or the treatment of alcohol dependence. As such, the present invention provides a family of 4',5'-dihydrospiro[piperidine-4,7'-thieno[2,3-c]pyran] compounds with high antagonist potency for the ORL-1 receptor, for use in the treatment of alcohol use disorders.

One aspect of the present invention provides a compound of Formula

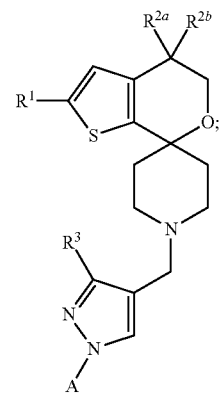

or a pharmaceutically acceptable salt thereof; for use in the treatment of an alcohol use disorder;
wherein
A is

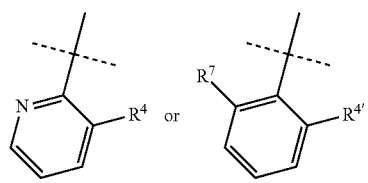

$R^1$ is fluoro or chloro;
$R^{2a}$ and $R^{2b}$ are each hydrogen or are each fluoro;
$R^3$ is hydrogen, methyl, hydroxymethyl, or ($C_1$-$C_3$) alkoxymethyl;
$R^4$ is selected from the group consisting of fluoro, chloro, cyano, cyanomethyl, ($C_1$-$C_3$) alkyl, cyclopropyl, hydroxymethyl, methoxy, cyclopropylmethoxy, aminocarbonylmethoxy, ($C_1$-$C_3$) alkoxymethyl, cyclopropyloxymethyl, cyclopropylmethoxymethyl, 1-hydroxy-1-methylethyl, aminocarbonyloxymethyl, methylaminocarbonyloxymethyl, dimethylaminocarbonyloxymethyl, aminocarbonyl, aminocarbonylmethyl, —$CH_2$—$NR^5R^6$, hydroxyimine, methoxyimine, morpholin-4-yl, morpholin-4-ylmethyl, $Ar^1$, —$CH_2Ar^1$, tetrahydrofuran-2-yl, 3-oxomorpholin-4-ylmethyl, 2-oxopyrrolidin-1-ylmethyl, and 2-oxopiperidin-1-ylmethyl;
$R^{4'}$ is selected from the group consisting of fluoro, chloro, cyano, cyanomethyl, ($C_1$-$C_3$) alkyl, cyclopropyl, hydroxymethyl, methoxy, methoxymethyl, aminocarbonyloxymethyl, methylaminocarbonyloxymethyl, dimethylaminocarbonyloxymethyl, methylcarbonyl, aminocarbonyl, methylaminocarbonyl, dimethylaminocarbonyl, —NR$^5$R$^6$, —CH$_2$—NR$^5$R$^6$, morpholin-4-yl, morpholin-4-ylmethyl, Ar$^2$, —CH$_2$Ar$^2$, 3,3-difluoroazetidin-1-ylmethyl, pyrrolidin-1-ylmethyl, 1-aminocyclopropyl, 1-methylaminocyclopropyl, and 1-dimethylaminocyclopropyl;

R$^5$ is hydrogen, C$_1$-C$_3$ alkyl, cyanomethyl, —C(O)CH$_3$, or aminocarbonylmethyl;

R$^{5'}$ is hydrogen, C$_1$-C$_4$ alkyl, cyclopropyl, hydroxyethyl, methoxyethyl, —C(O)CH$_3$, or —C(O)O(C$_1$-C$_3$) alkyl;

R$^6$ is hydrogen or methyl;

R$^7$ is hydrogen, fluoro, chloro, methyl, hydroxymethyl, or methoxy;

Ar$^1$ is a moiety selected from the group consisting of imidizol-1-yl, imidizol-2-yl, 2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1,2,4-oxadiazol-5-yl; and Ar$^2$ is a moiety selected from the group consisting of imidizol-1-yl, imidizol-2-yl, 2-methylimidizol-1-yl, 1-methylimidizol-2-yl, and 1,2,4-triazol-3-yl.

In further embodiments of this aspect of the invention the alcohol use disorder is alcohol dependence or alcohol abuse or both. In a further embodiment, the use is in simultaneous, separate, or sequential combination with another therapeutic ingredient.

In another aspect of the invention there is provided a pharmaceutical composition for treating an alcohol use disorder comprising a compound of Formula I, or a pharmaceutically acceptable salt thereof, and one or more pharmaceutically acceptable excipients, carriers, or diluents thereof. In another embodiment of this aspect of the invention there is provided a pharmaceutical composition for treating alcohol dependence or alcohol abuse or both, comprising a compound of Formula I, or a pharmaceutically acceptable salt thereof, and one or more pharmaceutically acceptable excipients, carriers, or diluents thereof. A further embodiment of this aspect of the invention provides a pharmaceutical composition comprising a compound according to Formula I, or pharmaceutically acceptable salt thereof, and at least one pharmaceutically acceptable carrier, exciepient or diluent, and optionally other therapeutic ingredients.

Another aspect of the present invention provides a method of treating an alcohol use disorder in a human comprising administering to a human in need of such treatment an effective amount of a compound of Formula I or a pharmaceutically acceptable salt thereof. Further embodiments of this aspect of the invention provide a method of treating alcohol dependence or alcohol abuse or both, comprising administering to a human in need of such treatment an effective amount of a compound of Formula I, or a pharmaceutically acceptable salt thereof.

Another aspect of this invention provides the use of a compound of Formula I, or a pharmaceutically acceptable salt thereof, in the manufacture of a medicament for the treatment of an alcohol use disorder. In other embodiments of this aspect of the invention the alcohol use disorder is alcohol dependence or alcohol abuse or both. Compounds for use in this invention are bases, and accordingly react with a number of organic and inorganic acids to form pharmaceutically acceptable salts. Pharmaceutically acceptable salts of each of the compounds of the present invention are contemplated within the scope of the present application. The term "pharmaceutically acceptable salt" as used herein, refers to any salt of a compound of Formula I that is substantially non-toxic to living organisms. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008). In one embodiment the salt is a tartrate salt. In another embodiment the salt is a HCl salt.

Preferred compounds for use in the present invention are compounds wherein:

1) R$^1$ is chloro;
2) R$^{2a}$ and R$^{2b}$ are each fluoro;
3) R$^1$ is chloro and R$^{2a}$ and R$^{2b}$ are each fluoro;
4) R$^1$ is fluoro and R$^{2a}$ and R$^{2b}$ are each hydrogen;
5) R$^3$ is hydrogen, methyl, hydroxymethyl, or methoxymethyl;
6) R$^3$ is methyl;
7) R$^3$ is hydroxymethyl;
8) R$^1$ is chloro, R$^{2a}$ and R$^{2b}$ are each fluoro, and R$^3$ is methyl;
9) R$^1$ is chloro, R$^{2a}$ and R$^{2b}$ are each fluoro, and R$^3$ is hydroxymethyl;
10) R$^4$ is fluoro, hydroxymethyl, methoxymethyl, or pyrazol-1-ylmethyl;
11) R$^4$ is fluoro;
12) R$^4$ is hydroxymethyl;
13) R$^4$ is methoxymethyl;
14) R$^4$ is pyrazol-1-ylmethyl;
15) any one of preferred embodiments 1) through 9) wherein R$^4$ is fluoro;
16) any one of preferred embodiments 1) through 9) wherein R$^4$ is hydroxymethyl;
17) any one of preferred embodiments 1) through 9) wherein R$^4$ is methoxymethyl;
18) any one of preferred embodiments 1) through 9) wherein R$^4$ is pyrazol-1-ylmethyl;
19) R$^7$ is hydrogen, fluoro, or chloro;
20) R$^7$ is fluoro;
21) R$^1$ is chloro, R$^{2a}$ and R$^{2b}$ are each fluoro, and R$^7$ is fluoro;
22) R$^1$ is chloro, R$^{2a}$ and R$^{2b}$ are each fluoro, R$^3$ is methyl, and R$^7$ is fluoro;
23) R$^1$ is chloro, R$^{2a}$ and R$^{2b}$ are each fluoro, R$^3$ is hydroxymethyl, and R$^7$ is fluoro;
24) R$^{4'}$ is fluoro, hydroxymethyl, methoxymethyl, methylcarbonyl or 2-methylimidazol-1-yl;
25) R$^{4'}$ is fluoro;
26) R$^{4'}$ is hydroxymethyl;
27) R$^{4'}$ is methoxymethyl;
28) R$^{4'}$ is methylcarbonyl;
29) R$^{4'}$ is 2-methylimidazol-1-yl;
30) any one of preferred embodiments 1) through 9) or 19) through 23) wherein R$^{4'}$ is fluoro;
31) any one of preferred embodiments 1) through 9) or 19) through 23) wherein R$^{4'}$ is hydroxymethyl;
32) any one of preferred embodiments 1) through 9) or 19) through 23) wherein R$^{4'}$ is methoxymethyl;
33) any one of preferred embodiments 1) through 9) or 19) through 23) wherein R$^{4'}$ is methylcarbonyl;
34) any one of preferred embodiments 1) through 9) or 19) through 23) wherein R$^{4'}$ is 2-methylimidazol-1-yl Certain preferred compounds for use in the methods and uses of the present invention are those in the following table and their pharmaceutically acceptable salts:

| Compound | Name | Structure |
|---|---|---|
| 1 | [2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol | 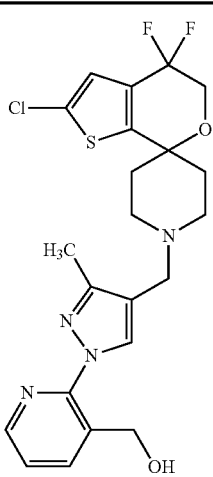 |
| 2 | 2-Chloro-4,4-difluoro-1'-[[1-(3-fluoro-2-pyridyl)-3-methyl-pyrazol-4-yl]methyl]spiro[5H-thieno[2,3-c]pyran-7,4'-piperidine] | 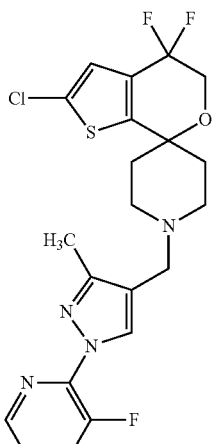 |
| 3 | 2-chloro-4,4-difluoro-1'-[[3-methyl-1-[3-(pyrazol-1-ylmethyl)-2-pyridyl]pyrazol-4-yl]methyl]spiro[5H-thieno[2,3-c]pyran-7,4'-piperidine] | 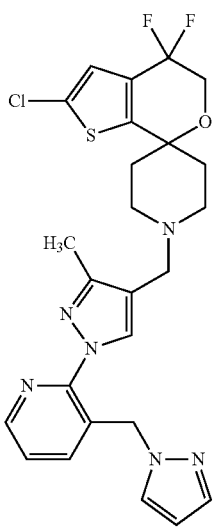 [SMILES: Cc1nn(-c2ncccc2Cn2cccn2)cc1CN1CCC2(CC1)OCC(F)(F)c1cc(Cl)sc12] |
| 4 | [4-[(2-chloro-4,4-difluoro-spiro[5H-thieno[2,3-c]pyran-7,4'-piperidine]-1'-yl)methyl]-1-(3-fluoro-2-pyridyl)pyrazol-3-yl]methanol | 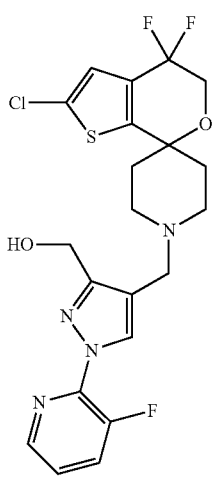 [SMILES: OCc1nn(-c2ncccc2F)cc1CN1CCC2(CC1)OCC(F)(F)c1cc(Cl)sc12] |
| 5 | 2-chloro-1'-[[1-(2,6-difluorophenyl)-3-methyl-pyrazol-4-yl]methyl]-4,4-difluoro-spiro[5H-thieno[2,3-c]pyran-7,4'-piperidine] | 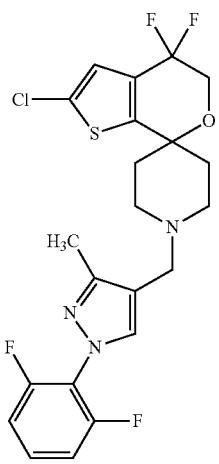 [SMILES: Cc1nn(-c2c(F)cccc2F)cc1CN1CCC2(CC1)OCC(F)(F)c1cc(Cl)sc12] |
| 6 | 1-(2-(4-((2'-chloro-4',4'-difluoro-4',5'-dihydrospiro[piperidine-4,7'-thieno[2,3-c]pyran]-1-yl)methyl)-3-methyl-1H-pyrazol-1-yl)-3-fluorophenyl)ethanone | 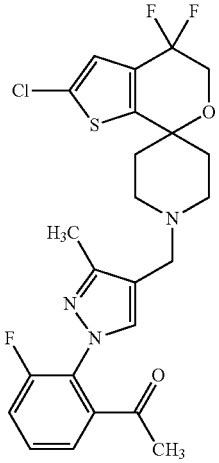 [SMILES: CC(=O)c1cccc(F)c1-n1cc(CN2CCC3(CC2)OCC(F)(F)c2cc(Cl)sc23)c(C)n1] |

| Compound | Name | Structure |
|---|---|---|
| 7 | 2-chloro-4,4-difluoro-1'-[[1-[2-fluoro-6-(2-methylimidazol-1-yl)phenyl]-3-methyl-pyrazol-4-yl]methyl] spiro[5H-thieno[2,3-c]pyran-7,4'-piperidine] | 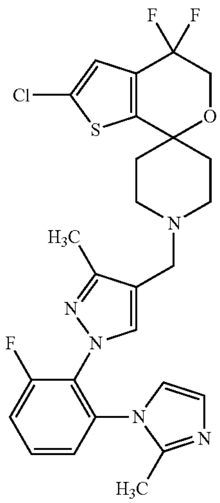 [SMILES: Cc1nn(-c2c(F)cccc2-n2ccnc2C)cc1CN1CCC2(CC1)OCC(F)(F)c1cc(Cl)sc12] |
| 8 | [4-[(2-chloro-4,4-difluoro-spiro[5H-thieno[2,3-c]pyran-7,4'-piperidine]-1'-yl)methyl]-1-(2,6-difluorophenyl)pyrazol-3-yl]methanol | 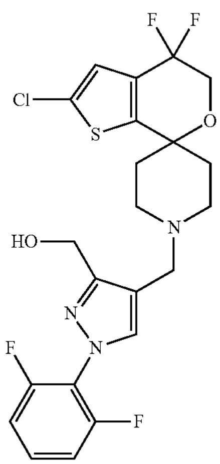 [SMILES: OCc1nn(-c2c(F)cccc2F)cc1CN1CCC2(CC1)OCC(F)(F)c1cc(Cl)sc12] |

Compounds wherein $R^{2a}$ and $R^{2b}$ are each fluoro are preferred because the compounds have a more favorable pharmacokinetic profile, being more stable to oxidative metabolism. This has the general effect of improving the oral bioavailability of the compounds.

The compounds for use in the present invention and methods of making them are known in the art and are characterized as potent and selective ORL-1 receptor antagonists. They can be prepared according to known synthetic schemes by methods well known and appreciated in the art. See for example WO 2011/060035 and WO 2011/060217.

Data generated in nonclinical animal studies support a role for ORL-1 receptor antagonists in the treatment of alcohol use disorders, such as alcohol abuse and alcohol dependence. Specifically it is found that certain ORL-1 receptor antagonists are effective in rodent models of alcohol use disorders. To demonstrate these characteristics of the present compounds, representative compounds may be run in the following in vivo assays:

Ethanol Self-Administration in Alcohol-Preferring Rats

Several lines of alcohol-preferring rats have been created through selective breeding techniques that meet the criteria for a validated animal model of alcoholism. Specifically, they voluntarily consume pharmacologically relevant levels of ethanol in the absence of food or water deprivation, they drink excessive levels of ethanol for its intoxicating effects, rather than taste, smell, or caloric value, maintain intoxication over long periods, work to gain access to ethanol, and with prolonged access, develop tolerance and dependence. (See e.g. Lester D and Freed E X (1973) Criteria for an animal model of alcoholism. *Pharmacology Biochemistry & Behavior* 1:103-107.) Such lines, including the Alcohol-Preferring (P) and the Marchigian Sardinian Alcohol-Preferring (msP) rats, are considered useful for assessing potential pharmacotherapies for alcohol-use disorders because they meet the above criteria and because agents that reduce alcohol consumption in humans, including naltrexone and acamprosate, reduce ethanol intake in these lines. Operant and free-choice self-administration procedures may be used to evaluate potential therapeutic anti-addiction activity of novel nociceptin/ORL1 antagonists in P and msP rats.

Operant Self-Administration in P rats:

Female P rats are obtained and pair-housed from a private colony (Taconic, Germantown, N.Y.). In order to reduce novelty-induced avoidance of ethanol, the water bottle on the homecage is replaced with a bottle containing 15% ethanol in water (v/v, in water) for two days prior to operant training. Throughout the rest of the experiment, rats receive ad libitum access to water and standard laboratory chow, with no further access to ethanol in the homecage.

Rats are trained to press a lever for ethanol reinforcement in daily 30-min sessions conducted in standard rat operant chambers contained within sound-attenuating chambers (MED Associates, Inc., St. Albans, Vt.). The chambers consist of two stainless steel and two clear Plexiglas walls. The floor grid of the operant chambers consists of 0.5 cm diameter stainless steel bars placed approximately 1.5 cm apart. Each operant chamber contains two retractable operant levers located approximately 6 cm above the grid floor and 13 cm apart. A recessed trough is located in the space between the levers, through which a dipper cup (0.1 mL capacity) is raised to deliver response-contingent ethanol (15%, v/v, in water). Upon a reinforced response, a stimulus light is illuminated above the lever on which the response was made throughout the 4-sec dipper cup access. Operation of the stimuli and behavioral responses are controlled and recorded by personal computer for offline analysis (MED Associates, Inc., St. Albans, Vt.).

During operant training, responses on either lever are considered correct responses and are rewarded with 0.1 mL ethanol reinforcement. Once rats learn to press a lever to obtain ethanol reward, the response contingency is changed so that responses made on one lever (active lever) are reinforced, using a fixed-ratio (FR)-1 schedule of reinforcement, while responses on the other (inactive) lever are not reinforced. Once stable baseline responding is reached on an FR-1 schedule of reinforcement, the response contingency is increased to FR-2 and then again to FR-3 so that 3 lever presses are required for each reinforcement. Once rats reach a stable level of responding on the FR-3 schedule, the response contingency is changed to a progressive ratio schedule of reinforcement, for which the response requirement is slowly increased throughout each experimental session such that rats must work progressively harder to receive each ethanol reward. Specifically, the response requirement is increased as follows: all rats begin each session at an FR-1 schedule of reinforcement; after three reinforcements, the schedule is increased to FR-2; after three reinforcements at that level, the schedule is increased by two to FR-4; after three reinforcements, the schedule is increased by two to FR-6; and so on (see for e.g. Oster S M, Toalston J E, Kuc K A, Pommer T J, Murphy J M, Lumeng L, Bell R L, McBride W J and Rodd Z A (2006) Effects of multiple alcohol deprivations on operant ethanol self-administration by high-alcohol-drinking replicate rat lines. *Alcohol* 38:155-164). Each session lasts a total of 30 min, after which, all stimuli are turned off and levers are retracted. At the end of the session, the number of responses on the active and inactive levers, and the breakpoint, which is defined as the highest FR value reached during the session are recorded. The amount of ethanol consumed is calculated from the number of active lever presses, and converted into g/kg EtOH consumed. Rats receive oral administration of vehicle or test compound in the dose range of 3, 10, or 30 mg/kg (3 mL/kg dose volume, dissolved in a vehicle consisting of 20% Captisol® in 25 mM phosphate buffer at pH=2), or the non-selective opioid receptor antagonist naltrexone (10 mg/kg) as a positive control, 60 min. prior to the session, using a within-subjects, crossover design (3-4 day washout between subsequent doses). On a separate occasion, rats receive oral administration of vehicle or 30 mg/kg test compound (1 mL/kg dose volume, dissolved in a vehicle consisting of 20% Captisol® in 25 mM phosphate buffer), 30 min prior to the session, using a crossover design.

Representative compounds are assayed essentially as described above and found to reduce ethanol-motivated responding, and therefore ethanol consumption, in P rats maintained on a progressive ratio schedule of reinforcement. Compounds 1 and 2 are tested essentially as described above and are found to reduce ethanol-motivated responding as in Table 1. Importantly, responses on the inactive lever are not affected by the ORL-1 antagonists (p>0.05), indicating lack of nonspecific motor side effects.

TABLE 1

| Compound | Dose | Mean Number of Lever Presses (Vehicle) | Mean Number of Lever Presses (Drug-treated) | Reduction vs. Vehicle |
|---|---|---|---|---|
| naltrexone | 10 | 432.5 | 106.33 | 75.4% |
| 1 (freebase) | 3 | | 412.58 | 4.6% |
| | 10 | | 330 | 23.7% |
| | 30 | | 191.25 | 55.8% |
| 2 (tartrate) | 30 | 376.23 | 143.31 | 61.9% |

(ANOVA analysis: Compound 1: $F_{(4, 55)} = 5.2$, $p = 0.001$; Compound 2: $F_{(1, 24)} = 16.8$, $p < 0.001$).

Stress-Induced Reinstatement in msP Rats:

Stress is a key trigger for relapse to drug- and alcohol-seeking in humans and rodents (Sinha R (2008) Chronic stress, drug use, and vulnerability to addiction. *Ann N Y Acad Sci* 1141:105-130), and can be modeled in rats using a stress-induced reinstatement procedure. In this procedure, stress-induced reinstatement of alcohol-seeking is elicited by administration of the alpha2 adrenoceptor antagonist yohimbine, a known pharmacological stressor (Le A D, Harding S, Juzytsch W, Funk D and Shaham Y (2005) Role of alpha-2 adrenoceptors in stress-induced reinstatement of alcohol seeking and alcohol self-administration in rats. *Psychopharmacology (Berl)* 179:366-373).

Male msP rats are obtained from the University of Camerino (Marche, Italy) and individually housed with ad libitum access to water and standard laboratory chow. Rats are trained to lever press for 10% ethanol in water (v/v) in standard operant chambers (MED Associates, Inc., St. Albans, Vt.) located in sound-attenuating, ventilated environmental cubicles. The chambers consist of two stainless steel and two clear Plexiglas walls. The floor grid of the operant chambers consists of 0.5 cm diameter stainless steel bars placed approximately 1.5 cm apart. Each operant chamber is equipped with a drinking reservoir 4 cm above the grid floor, with two retractable operant levers located approximately 3 cm on either side of the drinking receptacle. Fluid delivery, lever presses, and presentation of visual stimuli (illumination of a white house light) are controlled by an IBM compatible computer for offline analysis.

Rats are first trained to self-administer ethanol solution in 30-min daily operant sessions under a FR1 schedule of reinforcement, in which each response on the active lever results in delivery of 0.1 ml of ethanol. Each ethanol delivery is associated with a 5-sec time-out signalled by illumination of a white house light. Alcohol self-administration training continues until stable baseline responding is achieved. Once stable responding is achieved, animals are subjected to 30-min extinction sessions, during which responses at the lever activate the delivery mechanism but do not result in the delivery of ethanol. The procedure of each session is the same as ethanol self-administration sessions except that the lever responses are no longer reinforced. Animals are pre-treated with vehicle for 3 days before the initial administration of ORL-1 receptor antagonists in order to familiarize them with the oral administration procedure. The msP rats are then subjected to the reinstatement test conducted under the same extinction conditions. Reinstatement consists of oral administration of vehicle or test compound (3 or 30 mg/kg, n=10/group, solubilized in a 1:1 mixture of distilled water and 1M $H_3PO_4$, using gentle warming in a 45-60° C. water bath), followed 30-min later by intraperitoneal administration of yohimbine (2.0 mg/kg) 30-min before the operant session.

Representative compounds are assayed essentially as described above and found to dose-dependently reduce stress-induced reinstatement of ethanol-seeking. Importantly, inactive lever responses are unaffected by treatment, indicating the reduction of yohimbine-induced reinstatement was not due to nonspecific changes in motor activity. Compounds 1 and 2 are tested essentially as described and are found to reduce stress-induced reinstatement of ethanol-seeking as in Table 2.

TABLE 2

| Compound | Dose | Lever Presses - Last Extinction Day | Lever Presses - Yohimbine Reinstatement (Vehicle) | Avg Lever Presses (Drug-treated) | Reduction vs. Vehicle |
|---|---|---|---|---|---|
| 1 (Freebase) | 3 | 9.0 | 17.6 | 5 5 | 68 8% |
| | 30 | | | 4.8 | 72.7% |
| 2 (Tartrate) | 3 | 10.3 | 17.9 | 7 7 | 57 0% |
| | 30 | | | 5.5 | 69.3% |

ANOVA analysis: Compound 1 Active bar: $F_{(2, 27)} = 18.2$, $p < 0.0001$; Inactive bar: $F_{(2, 27)} = 0.2$, $p > 0.05$; Compound 2 Active bar: $F_{(2, 27)} = 18.16$, $p < 0.001$; Inactive bar: $F_{(2, 27)} = 1.2$, $p > 0.05$.

Free-Choice Ethanol Self-Administration in Alcohol-Preferring Rats:

P Rats:

In this procedure (modified from Rodd-Henricks Z A, McKinzie D L, Shaikh S R, Murphy J M, McBride W J, Lumeng L and Li T K (2000) Alcohol deprivation effect is prolonged in the alcohol preferring (P) rat after repeated deprivations. *Alcohol Clin Exp Res* 24:8-16), female P rats are obtained from a private colony (Taconic, Germantown, N.Y.), individually-housed with food, 15% ethanol (v/v, in water), and water available ad libitum, and maintained on a 12 hr. light/dark cycle (lights off at 16:00). The chambers are equipped with a force transduction system (TSE Systems, Bad Homburg, Germany) attached to the ethanol, water, and food receptacles to enable continuous monitoring of food and liquid consumption. Rats voluntarily consume 15% ethanol with a mean daily intake of roughly 5 g/kg for several months prior to drug testing. Rats are treated orally with vehicle or test compounds in the dose range of 3, 10, or 30 mg/kg (3 mL/kg dose volume, dissolved in a vehicle consisting of 20% Captisol® in 25 mM phosphate buffer at pH=2), or naltrexone (10 mg/kg, 1 mL/kg dose volume, dissolved in water) immediately prior to the onset of the dark cycle, using a within-subjects, crossover design (3-4 day washout between subsequent doses). In a separate experiment, rats receive oral administration of vehicle followed by 4 daily oral doses of vehicle or 30 mg/kg test compound immediately prior to the onset of the dark cycle, using a between-subjects design.

msP Rats:

In a separate study, male msP rats are obtained from a private colony (University of Camerino, Marche, Italy), individually-housed with food, 10% ethanol (v/v in water), and water available ad libitum, and maintained on a 12 hr. light/dark cycle. Ethanol and water are measured using graduated bottles to assess the volume of ethanol consumed (Economidou D, Fedeli A, Fardon R M, Weiss F, Massi M and Ciccocioppo R (2006) Effect of novel nociceptin/orphanin FQ-NOP receptor ligands on ethanol drinking in alcohol-preferring msP rats. *Peptides* 27:3299-3306.). Food intake is monitored by weighing the food receptacle. Once rats reach a stable baseline of voluntary ethanol consumption of 5-6 g/kg/day (approximately 4-5 months of age), rats are treated orally with test compounds in the dose range of 3 or 30 mg/kg in a formulation consisting of 1:1 distilled water: 1 M H$_3$PO$_4$ (1-5 mL/kg dose volume), one hour prior to onset of the dark cycle, using a within-subjects, crossover design (3-4 day washout between subsequent doses). Ethanol, water, and food are presented to the animals at the onset of the dark cycle, and consumption of food and fluids is measured at 2, 8, and 24 hr intervals.

Representative compounds are assayed essentially as described above and found to produce a selective dose-dependent reduction in ethanol self-administration in both P rats and msP rats with free-choice access to ethanol, without significantly affecting food or water intake. Compounds 1, 2, and 5 are assayed essentially as described and are found to significantly reduce ethanol self-administration, as shown in Table 3. In a separate experiment, Compound 1 is found to maintain suppression of ethanol intake in P rats throughout 4 days of once daily dosing without tachyphylaxis, as shown in Table 4.

TABLE 3

| Rat Strain | Compound | Dose | Mean EtOH Consumed in g/kg (Vehicle) | Mean EtOH Consumed in g/kg (Drug-treated) | Reduction vs. Vehicle | Timepoint measured |
|---|---|---|---|---|---|---|
| P | 1 (Freebase) | 3 | 4.73 | 3.54 | 25.2% | 12 hr |
|   |            | 10 |      | 3.67 | 22.4% | 12 hr |
|   |            | 30 |      | 1.50 | 68.3% | 12 hr |
|   | naltrexone | 10 |      | 3.30 | 30.2% | 12 hr |
| P | 2 (Tartrate) | 10 | 5.16 | 3.70 | 28.3% | 12 hr |
|   |            | 30 |      | 3.40 | 34.1% | 12 hr |
|   | naltrexone | 10 |      | 2.83 | 45.0% | 12 hr |
| P | 5 (Tartrate) | 3 | 5.17 | 4.39 | 15.0% | 12 hr |
|   |            | 10 |      | 4.05 | 21.5% | 12 hr |
|   |            | 30 |      | 3.74 | 27.6% | 12 hr |
|   | naltrexone | 10 |      | 3.31 | 36.0% | 12 hr |
| msP | 1 (Freebase) | 3 | 7.3 | 6.7 | 8.2% | 24 hr |
|     |            | 30 |     | 4.4 | 39.7% | 24 hr |
| msP | 2 (Tartrate) | 3 | 7.0 | 5.6 | 20.0% | 24 hr |
|     |            | 30 |     | 5   | 28.6% | 24 hr |

ANOVA analysis:
Compound 1: P rats, F (4, 40) = 6.03, p < 0.001, msP rats, F (2, 18) = 27.78, p < 0.001;
Compound 2: P rats, F (3, 52) = 6.6; p < 0.001, msP rats, F (2, 20) = 18.05, p < 0.001;
Compound 5: P rats, F (4, 28) = 3.48; p < 0.02; no significant affect on food or water intake, p > 0.05.

TABLE 4

| Cpd | Dose | Baseline EtOH Consumed in g/kg (day 1) | Mean EtOH Consumed in g/kg (day 2) | Mean EtOH Consumed in g/kg (day 3) | Mean EtOH Consumed in g/kg (day 4) | Mean EtOH Consumed in g/kg (day 5) |
|---|---|---|---|---|---|---|
| vehicle | vehicle | 4.94 | 4.38 | 5.28 | 4.89 | 5.43 |
| 1 (Freebase) | 30 | 4.36 (veh) | 1.59 | 2.02 | 2.69 | 2.50 |
| Reduction vs. vehicle = | | | 63.6% | 61.8% | 45.0% | 54.0% |

ANOVA analysis: F (2, 19) = 10.67, p < 0.001.

Ethanol-Stimulated Increases in Extracellular Dopamine Levels in the Nucleus Accumbens:

Ethanol and other drugs of abuse are known to increase extracellular levels of dopamine (DA) in the brain reward circuit, particularly the nucleus accumbens (Yoshimoto K, McBride W J, Lumeng L and Li T K (1992) Alcohol stimulates the release of dopamine and serotonin in the nucleus accumbens. *Alcohol* 9:17-22; Di Chiara G and Imperato A (1988) Drugs abused by humans preferentially increase synaptic dopamine concentrations in the mesolimbic system of freely moving rats. *Proc Natl Acad Sci USA* 85:5274-5278). The magnitude increase in nucleus accumbens DA levels directly correlate with subjective reports of pleasure and reward, and are related to abuse potential. Naltrexone, a marketed drug for the treatment of alcohol dependence, blocks ethanol-stimulated DA release in the nucleus accumbens (Gonzales R A and Weiss F (1998) Suppression of ethanol-reinforced behavior by naltrexone is associated with attenuation of the ethanol-induced increase in dialysate dopamine levels in the nucleus accumbens. *J Neurosci* 18:10663-10671).

Male Sprague-Dawley rats with a body weight of 260-300 g from Taconic Farms (Germantown, N.Y.) are implanted with a guide cannula (Bioanalytical Systems Inc, West Lafayette, Ind.) in the nucleus accumbens by the vendor 5-7 days before the experiment. Stereotaxic coordinates for the nucleus accumbens cannula are: A (anterior to bregma), 1.7 mm; L (lateral from the midsagittal suture, right side), 1.0 mm; and V (ventral from the dura surface), −6.0 mm (Paxinos and Watson, 1986). A concentric type probe (BR-2) from Bioanalytical Systems Inc. (West Lafayette, Ind.) is flushed with water and carefully inserted through the cannula about 16 hours before the experiment so that 2 mm of the membrane tip extends below the end of the guide cannula. The rat is then placed in a plastic test bowl to acclimate overnight. Based on methods modified from Melendez et al. (Melendez R I, Rodd-Henricks Z A, McBride W J and Murphy J M (2003), Alcohol stimulates the release of dopamine in the ventral pallidum but not in the globus pallidus: a dual-probe microdialysis study. *Neuropsychopharmacology* 28:939-946), the rat is connected to a fraction collection system for freely moving animals on the morning of the experiment (Raturn, BioAnalytical Systems Inc, West Lafayette, Ind.). The input tube of the dialysis probe is connected to a syringe pump (BeeHive and BabyBee, Bioanalytical Systems Inc, West Lafayette, Ind.) which delivers an artificial cerebrospinal fluid (150 mM NaCl, 3 mM KCl, 1.7 mM CaCl2 and 0.9 mM MgCl2 (pH 6.0)) to the probe at a final collection rate of 1.5 µL/min. The output tubes from the rats are attached to a refrigerated fraction collector (Bioanalytical Systems Inc, West Lafayette, Ind.). After a period of about an hour at an initial perfusion rate of 5.0 µL/min, the flow rate is decreased to 2.0 µL/min for equilibration of the probe and establishment of stable baseline levels for 1 hour, then collection of 20 minute fractions is started. Four baseline samples are collected before injection of any drugs.

Test compound is administered orally at 30 mg/kg (2 ml/kg dose volume, dissolved in a vehicle consisting of 20% Captisol® in 25 mM phosphate buffer at pH=3). The compound is administered either alone (10 min into the $4^{th}$ sample; 0 min time point) or in combination with ethanol (10 min into the $1^{st}$ sample; −60 min time point). Ethanol is administered intraperitoneally (ip) at a dose of 1.1 g/kg in a 15% (v/v) solution in 0.9% saline in a volume of 2.9 ml per rat. Ethanol is administered 10 min into the $4^{th}$ sample (0 min time point). Dialysate samples are transferred to an Alcott 718 Autosampler/Injector with the sample cooling tray set to 5° C. (Alcott Inc., Norcross, Ga.). An HPLC analytical method simultaneously detects norepinephrine (NE), dopamine (DA), and serotonin (5-HT) and their metabolites 3,4-dihydroxyphenylacetic acid (DOPAC), homovanillic acid (HVA), 3-methoxy-4-hydroxyphenylglycol (MHPG), and the serotonin metabolite, 5-hydroxyindoleacetic acid (5-HIAA) in the same dialysates. A BDS-Hypersil 3 µm C18 analytical column (2×150 mm from Thermo-Fisher) with a ten-port HPLC valve and a 20 µL sample loop is used in configuration with a small sample clean-up column (BDS-Hypersil 3 µm C18, 2×10 mm), which traps a late-eluting peak contained in the dialysate samples. The mobile phase for both columns is the same and consists of 75 mM sodium phosphate monobasic, 350 mg/L 1-octanesulfonic acid sodium salt, 0.5 mM EDTA, 0.8% tetrahydrofuran (HPLC grade, inhibitor-free) and 8% acetonitrile at pH 3 (adjusted with phosphoric acid). The flow rate for both columns is 0.20 mL/min. The analytical column is maintained at 40° C. with a column heater, while the sample cleanup column is mounted on the ten-port valve at room temperature. An electrochemical detector (EG & G PARC, Princeton, N.J.) with dual glassy carbon electrodes is used (E1=680 mV, E2=100 mV, range=0.5 nA on both electrodes). The metabolites are detected at E1 while NE and DA are detected at E2. Since extracellular DOPAC, HVA and 5-HIAA levels are much higher than DA and NE levels, the DOPAC, HVA and 5-HIAA peaks are analyzed by utilizing the 10 volt output on the EG&G detector which sends a separate channel to the computer that allows the metabolite peaks to stay on scale. The data of all three channels is collected using an EZChrom chromatography data system (Scientific Software, San Ramon, Callif.) which calculated peak heights and sample concentrations. The sensitivity for NE, DA and 5HT is 0.1 pmol/mL dialysate or 2 fmol/sample (20 µL).

Vehicle+ethanol (1.1 g/kg, IP) increases extracellular levels of DA in the rat nucleus accumbens to approximately 125-130% of baseline levels, an effect similar to that reported in the literature and produced to varying degrees by all drugs of abuse. Representative compounds are assayed essentially as described above and are found to prevent the increase in extracellular DA concentration in the rat nucleus accumbens.

Importantly, when dosed in the absence of ethanol, the compounds have no effect on extracellular levels of DA in the nucleus accumbens. Compound 1 is assayed essentially as described above and is found to prevent the increase in extracellular DA concentrations in the nucleus accumbens, as shown in Table 5.

TABLE 5

| Treatment Group | Mean DA level (% of baseline) during 120 min period post-EtOH injection | Reduction of DA response relative to Vehicle |
|---|---|---|
| Vehicle + Vehicle | 105.76 | n/a |
| Vehicle + EtOH | 123.45 | n/a |
| 1 (Freebase) + Vehicle | 98.53 | n/a |
| 1 (Freebase) + EtOH | 102.78 | 88.16% |

ANOVA analysis: Compound 1 + EtOH to vehicle + EtOH: F (3, 28) = 7.25, p = 0.001. Compound 1 + vehicle to vehicle + vehicle: p > 0.05.

Based on the data presented herein, compounds of the present invention are expected to demonstrate efficacy in treating alcohol use disorders.

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, intranasal, transdermal, subcutaneous, intravenous, intramuscular, and pulmonary. Such pharmaceutical compositions and processes for preparing them are well known in the art. See, e.g., Remington: The Science and Practice of Pharmacy (University of the Sciences in Philadelphia, ed., $21^{st}$ ed., Lippincott Williams & Wilkins Co., 2005).

The compositions are preferably formulated in a unit dosage form, each dosage containing from about 0.1 to about 500 mg, more usually about 1.0 to about 200 mg, as for example between about 5 and 50 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.01 to about 50 mg/kg, more usually from about 0.05 to 5.0 mg/kg, and as for example between 0.1 and 1.0 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

I claim:
1. A method of treating an alcohol use disorder in a human comprising administering to a human in need of such treatment an effective amount of a compound of the formula:

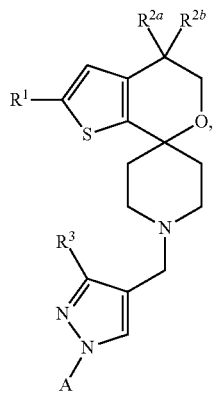

or a pharmaceutically acceptable salt thereof;
wherein
A is

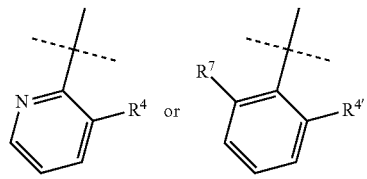

$R^1$ is fluoro or chloro;
$R^{2a}$ and $R^{2b}$ are each hydrogen or are each fluoro;
$R^3$ is hydrogen, methyl, hydroxymethyl, or ($C_1$-$C_3$) alkoxymethyl;
$R^4$ is selected from the group consisting of fluoro, chloro, cyano, cyanomethyl, ($C_1$-$C_3$) alkyl, cyclopropyl, hydroxymethyl, methoxy, cyclopropylmethoxy, aminocarbonylmethoxy, ($C_1$-$C_3$) alkoxymethyl, cyclopropyloxymethyl, cyclopropylmethoxymethyl, 1-hydroxy-1-methylethyl, aminocarbonyloxymethyl, methylaminocarbonyloxymethyl, dimethylaminocarbonyloxymethyl, aminocarbonyl, aminocarbonylmethyl, —$CH_2$—$NR^5R^6$, hydroxyimine, methoxyimine, morpholin-4-yl, morpholin-4-ylmethyl, $Ar^1$, —$CH_2Ar^1$, tetrahydrofuran-2-yl, 3-oxomorpholin-4-ylmethyl, 2-oxopyrrolidin-1-ylmethyl, and 2-oxopiperidin-1-ylmethyl;
$R^{4'}$ is selected from the group consisting of fluoro, chloro, cyano, cyanomethyl, ($C_1$-$C_3$) alkyl, cyclopropyl, hydroxymethyl, methoxy, methoxymethyl, aminocarbonyloxymethyl, methylaminocarbonyloxymethyl, dimethylaminocarbonyloxymethyl, methylcarbonyl, aminocarbonyl, methylaminocarbonyl, dimethylaminocarbonyl, —$NR^5R^6$, —$CH_2$—$NR^5R^6$, morpholin-4-yl, morpholin-4-ylmethyl, $Ar^2$, —$CH_2Ar^2$, 3,3-difluoroazetidin-1-ylmethyl, pyrrolidin-1-ylmethyl, 1-aminocyclopropyl, 1-methylaminocyclopropyl, and 1-dimethylaminocyclopropyl;
$R^5$ is hydrogen, $C_1$-$C_3$ alkyl, cyanomethyl, —$C(O)CH_3$, or aminocarbonylmethyl;
$R^{5'}$ is hydrogen, $C_1$-$C_4$ alkyl, cyclopropyl, hydroxyethyl, methoxyethyl, —$C(O)CH_3$, or —$C(O)O(C_1$-$C_3)$ alkyl;
$R^6$ is hydrogen or methyl;
$R^7$ is hydrogen, fluoro, chloro, methyl, hydroxymethyl, or methoxy;
$Ar^1$ is a moiety selected from the group consisting of imidizol-1-yl, imidizol-2-yl, 2-methylimidizol-1-yl, pyrazol-1-yl, 1,2,3-triazol-1-yl; 1,2,3-triazol-2-yl; 1,2,4-triazol-1-yl, isoxazol-3-yl, oxazol-5-yl, and 3-methyl-1,2,4-oxadiazol-5-yl; and
$Ar^2$ is a moiety selected from the group consisting of imidizol-1-yl, imidizol-2-yl, 2-methylimidizol-1-yl, 1-methylimidizol-2-yl, and 1,2,4-triazol-3-yl.

2. The method of claim 1 wherein $R^{2a}$ and $R^{2b}$ are each fluoro.

3. The method of claim 2 wherein $R^1$ is chloro and $R^3$ is methyl or hydroxymethyl.

4. The method of claim 3 wherein $R^3$ is methyl.

5. The method of claim 1 wherein the compound is
[2-[4-[(2-chloro-4,4-difluoro-spiro[5H-thieno[2,3-c]pyran-7,4'-piperidine]-1'-yl)methyl]-3-methyl-pyrazol-1-yl]-3-pyridyl]methanol,
2-Chloro-4,4-difluoro-1'-[[1-(3-fluoro-2-pyridyl)-3-methyl-pyrazol-4-yl]methyl]spiro[5H-thieno[2,3-c]pyran-7,4'-piperidine], or
2-Chloro-1'-[[1-(2,6-difluorophenyl)-3-methyl-pyrazol-4-yl]methyl]-4,4-difluoro-spiro[5H-thieno[2,3-c]pyran-7,4'-piperidine], or a pharmaceutically acceptable salt thereof.

6. The method of claim 1 wherein the compound is [2-[4-[(2-Chloro-4,4-difluoro-spiro[5H-thieno[2,3-c]pyran-7,4'-piperidine]-1'-yl)methyl]-3-methyl-pyrazol-1-yl]-3-pyridyl]methanol, or a pharmaceutically acceptable salt thereof.

7. The method of claim 1 wherein the alcohol use disorder is alcohol dependence.

8. The method of claim 2 wherein the alcohol use disorder is alcohol dependence.

9. The method of claim 5 wherein the alcohol use disorder is alcohol dependence.

10. The method of claim 6 wherein the alcohol use disorder is alcohol dependence.

11. The method of claim 1 wherein the alcohol use disorder is alcohol abuse.

12. The method of claim 2 wherein the alcohol use disorder is alcohol abuse.

13. The method of claim 5 wherein the alcohol use disorder is alcohol abuse.

14. The method of claim 6 wherein the alcohol use disorder is alcohol abuse.

* * * * *